US006320078B1

(12) United States Patent
Suzuki et al.

(10) Patent No.: US 6,320,078 B1
(45) Date of Patent: Nov. 20, 2001

(54) METHOD OF PRODUCING BENZAMIDE DERIVATIVES

(75) Inventors: Tsuneji Suzuki; Tomoyuki Ando; Katsutoshi Tsuchiya, all of Chiba; Hiroki Ishibashi, Fukuoka, all of (JP)

(73) Assignee: Mitsui Chemicals, Inc. (JP)

( * ) Notice: Subject to any disclaimer, the term of this patent is extended or adjusted under 35 U.S.C. 154(b) by 0 days.

(21) Appl. No.: 09/359,368

(22) Filed: Jul. 23, 1999

(30) Foreign Application Priority Data

Jul. 24, 1998 (JP) .................................................. 10-209738

(51) Int. Cl.[7] ......................... C07C 233/05; C07C 231/02
(52) U.S. Cl. ......................... 564/163; 564/134; 546/290; 546/309
(58) Field of Search ................................ 564/163, 134; 546/290, 309

(56) References Cited

U.S. PATENT DOCUMENTS 5,767,270 * 6/1998 Bhat ..................................... 548/253

FOREIGN PATENT DOCUMENTS

| 0 314 483 A | 5/1989 | (EP) . |
| WO97/23443 | 7/1997 | (WO) . |

OTHER PUBLICATIONS

Kolkmann et al, Tetrahedron Letters, vol. 26, No. 14, pp. 1703–1704, 1985.*

Keana et al, J. of Fluorine Chem., vol. 43, pp. 151–154, 1989.*

Stadler, P.A. et al, "A Mild, Facile Method for the Preparation of Amino–Esters", Helvetica Chimica Acta, vol. 68, No. 6, 1985, pp. 1644–1646, XP000973828.

* cited by examiner

Primary Examiner—Shailendra Kumar
(74) Attorney, Agent, or Firm—Burns, Doane, Swecker, & Mathis, L.L.P.

(57) ABSTRACT

In the case that a selectively monoacylated phenylenediamine derivative which is useful as any of medicines, agricultural chemicals, animal drugs and the intermediates of chemicals is prepared by reacting a benzoic acid derivative with a phenylenediamine derivative, the benzoic acid derivative is converted into a benzoyl imidazole derivative and this benzoyl imidazole derivative is then reaction with the phenylenediamine derivative, whereby the improvement of a preparation efficiency and the high selectivity of the monoacylation can be achieved, the steps of protection and deprotection being omitted.

11 Claims, No Drawings

METHOD OF PRODUCING BENZAMIDE DERIVATIVES

BACKGROUND OF THE INVENTION

1. Field of the Invention

The present invention relates to a process for preparing a selectively-monoacylated phenylenediamine derivative as a benzamide derivative.

2. Description of the Related Art

Monoacylated phenylenediamine derivatives are very important compounds as chemicals, medicines, agricultural chemicals, animal drugs and intermediates thereof, and their precursors are also very important compounds.

A reaction between a benzoic acid derivative and an amine derivative to synthesize an amide derivative is one of most fundamental reactions in conventional organic synthesis techniques, and many technical accumulations and results are known. However, when the amine derivative has two or more amino groups, methods for selectively acylating one amino group alone are limited. For example, as in the case that one amino group is an aliphatic amino group and the other is an aromatic amino group, if two amino groups are noticeably different in reactivity, it is easy to selectively acylate the amino group alone which has a higher reactivity than the other.

On the other hand, if a large difference of the reactivity is not present between two amino groups as in the case of a phenylenediamine derivative, a monoacylation reaction and in succession a diacylation reaction occur, so that it is difficult to obtain a target compound monoacylated with a good selectivity. For example, since the phenylenediamine has generally two amino groups having similar reactivites, when an acid chloride derivative which is prevalent as an acylating agent is reacted with the phenylenediamine, a diacylated phenylenediamine derivative is produced in large quantities as a by-product under usual reaction conditions such as at room temperature, so that a purity of a monoacylated phenylenediamine derivative is low and its yield is also low.

Furthermore, several methods have also been contrived in which an activator other than the acid chloride is used as the acylating agent to heighten the selectivity, and some reports regarding the monoacylation reaction of the phenylenediamine derivative have been presented. However, such methods are accompanied with various problems, and hence they cannot be applied to the mass production of the monoacylated phenylenediamine derivatives which are useful as chemicals, medicines, agricultural chemicals, animal drugs and intermediates thereof. For example, Arnand et al. have reported on pages 553 to 554 of Synlett in 1994 that a dicarboxylic acid is activated with thiazolidine-2-thione and then reacted with a phenylenediamine derivative to selectively obtain its monoacylated product. However, this reaction has some problems, and for example, a reaction substrate is a peculiar dicarboxylic acid and the reaction must be carried out at room temperature for a long period of 4 days. In addition, Shalaby et al. have also reported on pages 9045 to 9048 of J. Org. Chem., Vol. 61 in 1996 that a carboxylic acid is activated with isobutyl chloroformate and then reacted with a 1,2-phenylenediamine derivative at −20° C., but the phenylenediamine derivative is limited to 4-nitro-1,2-phenylenediamine having a special reactivity. Similarly, Goeker et al. have reported a reaction with methyl 3,4-diaminobenzoate on pages 1767 to 1773 of J. Heterocyclic Chem., Vol. 32 in 1995, and Edmundson et al. have reported a reaction with 2,6-dibromo-1,4-phenylenediamine on pages 2452 to 2453 of J.C.S.(C) in 1971. These methods reported by them are limited to the reactions on substrates in which a difference of the reactivity is caused between two amino groups by a substituent.

That is to say, in order to obtain the monoacylated phenylenediamine derivative with a high selectivity, there have been heretofore required special conditions such as the employment of such a limited structure so as to create a difference of the reactivity between two amino groups; the use of a large amount of the phenylenediamine derivative; or the execution of a reaction at an extremely low temperature; i.e., no general-purpose reaction suitable for the mass production is known. Accordingly, as described in Japanese Patent Laid-Open (Kokai) No. 152462/1998 and the like, it has heretofore been general that one amino group of the phenylenediamine derivative is protected, and an unprotected amino group alone is acylated, followed by removing the protective group, i.e., deprotection, to synthesize the monoacylated phenylenediamine derivative. In this synthesis technique, however, there are required the two steps of the protection and the deprotection which are not inherently necessary for the manufacture of the monoacylated phenylenediamine derivative as a useful skeleton, and for a higher efficiency of the manufacture, it has been very important to omit these additional steps.

SUMMARY OF THE INVENTION

An object of the present invention is to obtain, with a high selectivity, a monoacylated phenylenediamine derivative which is a skeleton useful as any of medicines, agricultural chemicals, animal drugs, chemicals and intermediates thereof by reacting an unprotected phenylenediamine derivative with a benzoic acid derivative without requiring a process including the steps for protection and deprotection in the manufacture of the monoacylated phenylenediamine derivative.

The present inventors have intensively investigated with the intention of achieving the above-mentioned object, and as a result, it has been found that when a benzoic acid derivative is converted into a benzoylimidazole derivative and is then reacted with a phenylenediamine derivative, the reaction can proceed promptly with a high selectivity under moderate conditions. Furthermore, it has also been found that in the case of the reaction with the less reactive phenylenediamine derivative, an acid can be added to the reaction system, whereby the reaction proceeds promptly under the moderate conditions to obtain the desired monoacylated phenylenediamine derivative with a high selectivity. On the basis of these findings, the present invention has been completed.

That is to say, the first aspect of a process for preparing a selectively monoacylated phenylenediamine derivative according to the present invention comprises the steps of converting, into a benzoylimidazole derivative, a benzoic acid derivative represented by the formula (1):

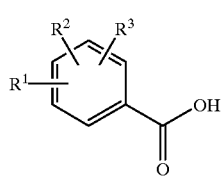

(1)

wherein $R^1$ and $R^2$ are each independently a hydrogen atom, or a substituent selected form the group consisting of halogen atom, an alkyl group having 1 to 4 carbon atoms, an alkoxy group having 1 to 4 carbon atoms, an acyl group having 1 to 4 carbon atoms, an acylamino group having 1 to 4 carbon atoms, an alkylthio group having 1 to 4 carbon atoms, a perfluoroalkyl group having 1 to 4 carbon atoms, a perfluoroalkyloxy group having 1 to 4 carbon atoms and an alkoxycarbonyl group having 1 to 4 carbon atoms, which substituent is located at an optional position on the benzene ring; and $R^3$ is a hydrogen atom or a substituent which is located at the other optional position than $R^1$ and $R^2$ on the benzene ring and is represented by the formula (2)

$$A\text{—}X\text{—}Q\text{—}(CH_2)_n\text{—} \qquad (2)$$

wherein A is a phenyl group or a heterocyclic ring which may be substituted by 1 to 4 groups selected from the group consisting of a halogen atom, a nitro group, a cyano group, an alkyl group having 1 to 4 carbon atoms, an alkoxy group having 1 to 4 carbon atoms, an acyl group having 1 to 4 carbon atoms, an acylamino group having 1 to 4 carbon atoms, an alkylthio group having 1 to 4 carbon atoms, a perfluoroalkyl group having 1 to 4 carbon atoms, a perfluoroalkyloxy group having 1 to 4 carbon atoms or an alkoxycarbonyl group having 1 to 4 carbon atoms, a phenyl group and a heterocyclic ring; X is a direct bond or one of structures represented by the formulae (3-1) to (3-7) in the formula group (3):

(3)

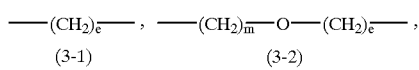
(3-1)      (3-2)

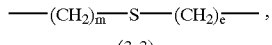
(3-3)

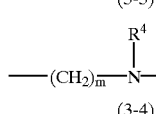
(3-4)

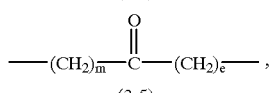
(3-5)

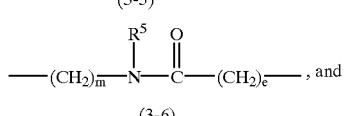
(3-6)

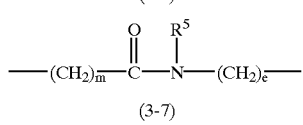
(3-7)

wherein e is an integer of 1 to 4; m is an integer of 0 to 4; $R^4$ is an alkyl group having 1 to 4 carbon atoms which may be substituted or an acyl group represented by the formula (4)

(4)

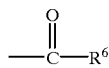

wherein $R_6$ an alkyl group having 1 to 4 carbon atoms, a perfluoroalkyl group having 1 to 4 carbon atoms, a phenyl group or a heterocyclic ring, which may be substituted;

$R^5$ is a hydrogen atom or an alkyl group having 1 to 4 carbon atoms, which may be substituted;

Q is a substituent represented by any of the formulae (5-1) to (5-9) in the formula group (5):

(5)

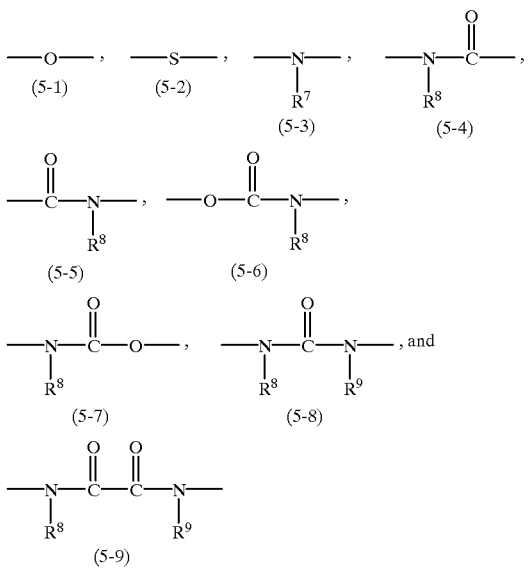

wherein $R^7$ is an alkyl group having 1 to 4 carbon atoms which may be substituted, or an acyl group represented by the formula (6)

(6)

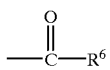

wherein $R^6$ is as defined above; $R^8$ and $R^9$ are each independently a hydrogen atom or an alkyl group having 1 to 4 carbon atoms which may be substituted;

and n is an integer of 0 to 4, and then reacting the benzoylimidazole derivative with a phenylenediamine derivative represented by the formula (7)

(7)

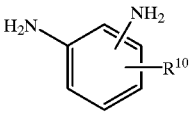

wherein $R^{10}$ is a hydrogen atom, or a halogen atom, a hydroxyl group, an alkyl group having 1 to 4 carbon atoms, an alkoxy group having 1 to 4 carbon atoms, an acyl group having 1 to 4 carbon atoms, an acylamino group having 1 to 4 carbon atoms, an alkylthio group having 1 to 4 carbon atoms, a perfluoroalkyl group having 1 to 4 carbon atoms, a perfluoroalkyloxy group having 1 to 4 carbon atoms or an alkoxycarbonyl group having 1 to 4 carbon atoms which is located at an optional position on the benzene ring, and one of the amino groups is located at a remaining optional position on the benzene ring.

The second aspect of the preparation method according to the present invention comprises the steps of converting, into a benzoylimidazole derivative, a benzoic acid derivative represented by the formula (1)

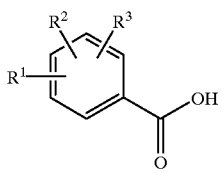

(1)

wherein $R^1$, $R^2$ and $R^3$ are as defined above, and then reacting the resultant benzoylimidazole derivative with a phenylenediamine derivative represented by the formula (7)

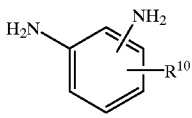

(7)

wherein $R^{10}$ is as defined above, in the presence of an acid for activation of the reaction.

The third aspect of the preparation method according to the present invention is directed to the preparation process of the first or the second aspect wherein the benzoic acid derivative is represented by the formula (8)

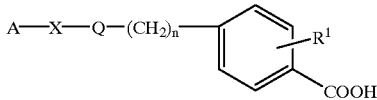

(8)

wherein A, X, Q, n and $R^1$ are as defined above.

The fourth aspect of the preparation method according to the present invention is directed to the preparation process of the third aspect wherein the substituent represented by A in the formula (8) is a pyridine ring or a condensed pyridine ring, which may be substituted.

The fifth aspect of the preparation method according to the present invention is directed to the preparation process of the fourth aspect wherein n is an integer of 1 to 4.

The sixth aspect of the preparation method according to the present invention is directed to the preparation process of the fifth aspect wherein $R^1$ is a hydrogen atom.

The seventh aspect of the preparation method according to the present invention is directed to the preparation process of the first or the second aspect wherein the benzoic acid derivative is represented by the formula (9):

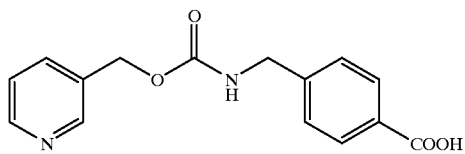

(9)

The eighth aspect of the preparation method according to the present invention is directed to the preparation process of the first or the second aspect wherein the benzoic acid derivative is represented by the formula (10):

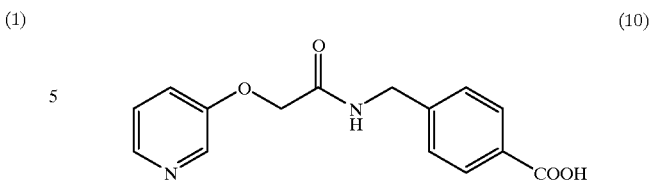

(10)

The ninth aspect of the preparation method according to the present invention is directed to the preparation process of the first or the second aspect wherein the benzoic acid derivative is represented by the formula (11):

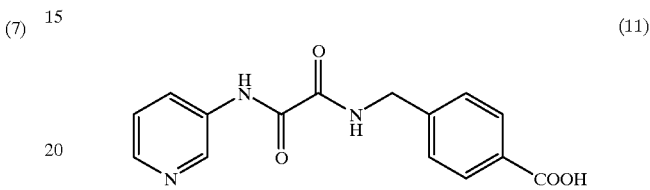

(11)

The tenth aspect of the preparation method according to the present invention is directed to the preparation process of any one of the first to the ninth aspect wherein the phenylenediamine derivative of a reaction material is represented by the formula (12)

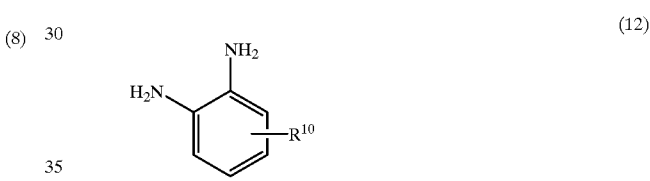

(12)

wherein $R^{10}$ is as defined above.

The eleventh aspect of the preparation method according to the present invention is directed to the preparation process of the tenth aspect wherein $R^{10}$ of the formula (12) is a hydrogen atom.

The first aspect of compounds according to the present invention is directed to compounds represented by the formula (13) and salts thereof

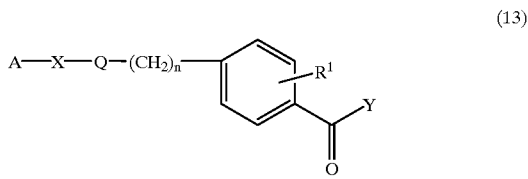

(13)

wherein A, X, Q, n and $R^1$ are as defined above; and Y is OH, Cl or a 1-imidazolyl group.

The second aspect of the compounds according to the present invention is directed to the compounds of the first aspect wherein A of the formula (13) is a heterocyclic ring which may be substituted.

The third aspect of the compounds according to the present invention is directed to the compounds of the first aspect wherein A of the formula (13) is a pyridine ring or a condensed pyridine ring, which may be substituted.

The fourth aspect of the compounds according to the present invention is directed to the compounds of the third aspect wherein n of the formula (13) is an integer of 1 to 4.

The fifth aspect of the compounds according to the present invention is directed to the compounds of the fourth aspect wherein $R^1$ of the formula (13) is a hydrogen atom.

The sixth aspect of the compounds according to the present invention is directed to the compounds of any one of the first to the fifth aspect wherein X of the formula (13) is a direct bond.

The seventh aspect of the compounds according to the present invention is directed to the compounds of any one of the first to the fifth aspect wherein X of the formula (13) is represented by the formula (14)

 (14)

wherein e is as defined above.

The eighth aspect of the compounds according to the present invention is directed to the compounds of any one of the first to the fifth aspect wherein X of the formula (13) is represented by any of the formulae (15-1) to (15-3) in the formula group (15):

(15)

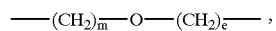

(15-1)

 and (15-2)

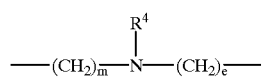

(15-3)

wherein e, m and $R^4$ are as defined above.

The ninth aspect of the compounds according to the present invention is directed to the compounds of any one of the first to the fifth aspect wherein X of the formula (13) is represented by any of the formulae (16-1) to (16-3) in the formula group (16):

(16)

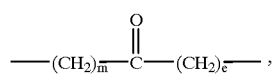

(16-1)

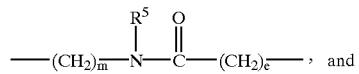 and (16-2)

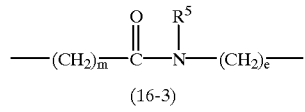

(16-3)

wherein e, m and $R^5$ are as defined above.

The tenth aspect of the compounds according to the present invention is directed to the compounds of any one of the first to the ninth aspect which are benzoic acid derivatives and salts thereof in which Y of the formula (13) is OH.

The eleventh aspect of the compounds according to the present invention is directed to the compounds of any one of the first to the ninth aspect which are benzoyl imidazole derivatives and salts thereof in which Y of the formula (13) is a 1-imidazolyl group.

The twelfth aspect of the compounds according to the present invention is directed to the compounds of any one of the first to the ninth aspect which are benzoyl chloride derivatives and salts thereof in which Y of the formula (13) is Cl.

Another aspect of the compounds according to the present invention is directed to a benzoic acid derivative represented by the formula (9)

(9)

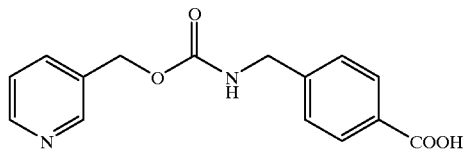

and salts thereof.

Another aspect of the compounds according to the present invention is directed to a benzoic acid derivative represented by the formula (10):

(10)

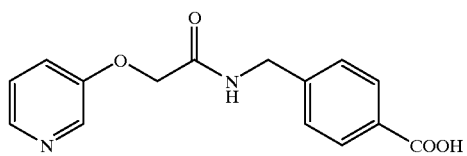

and salts thereof.

Another aspect of the compounds according to the present invention is directed to a benzoic acid derivative represented by the formula (11)

(11)

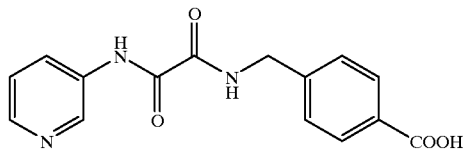

and salts thereof.

Another aspect of the compounds according to the present invention is directed to benzoyl imidazole derivatives represented by the formulae (17-1) to (17-3) in the fomula group (17), respectively:

(17)

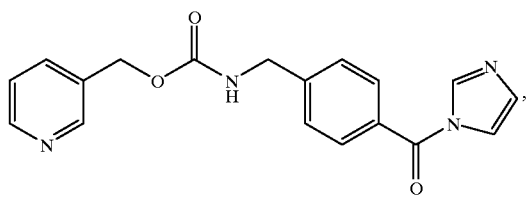

(17-1)

-continued

[Structure (17-2)]

[Structure (17-3)]

and salts thereof.

Another aspect of the compounds according to the present invention is directed to benzoyl chloride derivatives represented by the formulae (18-1) to (18-3) in the formula group (18):

(18)

[Structure (18-1)]

[Structure (18-2)]

[Structure (18-3)]

and salts thereof.

Another aspect of the preparation process according to the present invention is directed to an efficient preparation process of a benzoic acid derivative represented by the above-mentioned formula (9) which comprises the step of reacting 4-aminomethylbenzoic acid and 3-pyridinemethanol with N,N'-carbonyldiimidazole or phosgene without protection.

According to the present invention, there can be obtained, with a high selectivity, a monoacylated phenylenediamine derivative which is a skeleton useful as any of medicines, agricultural chemicals, animal drugs, chemicals and intermediates thereof by reacting an unprotected phenylenediamine derivative with a benzoic acid derivative without requiring a process including the steps for protection and deprotection in the manufacture of the monoacylated phenylenediamine derivative.

DETAILED DESCRIPTION OF THE
INVENTION AND PREFERRED
EMBODIMENTS

Next, the present invention will be described in detail.

"1 to 4 carbon atoms" referred to in the present invention means the number of carbon atoms per unit substituent. That is to say, for example, a dialkyl substitution means that it includes 2 to 8 carbon atoms.

A heterocyclic ring in each of compounds represented by the formulae (2), (8) and (13) means a monocyclic type heterocyclic ring or a bicyclic type heterocyclic ring comprising a five-membered ring or a six-membered ring including 1 to 4 of nitrogen atoms, oxygen atoms or sulfur atoms. Examples of the monocyclic type heterocyclic ring include pyridine, pyrazine, pyrimidine, pyridazine, thiophene, furan, pyrrole, pyrazole, isoxazole, isothiazole, imidazole, oxazole, thiazole, piperidine, piperazine, pyrrolidine, quinuclidine, tetrahydrofuran, morpholine and thiomorpholine, and examples of the bicyclic type heterocyclic ring include condensed pyridine rings such as quinoline, isoquinoline, naphthyridine, propyridyne, thienopyridine, pyrrolopyridine, oxazolopyridine, imidazolopyridine and thiazolopyridine, benzofuran, benzothiophene and benzoyl imidazole.

Examples of a halogen atom include a fluorine atom, a chlorine atom, a bromine atom and an iodine atom.

Examples of an alkyl group having 1 to 4 carbon atoms include a methyl group, an ethyl group, an n-propyl group, an isopropyl group, an n-butyl group, an isobutyl group, a sec-butyl group and a tert-butyl group.

Examples of an alkoxy group having 1 to 4 carbon atoms include a methoxy group, an ethoxy group, an n-propoxy group, an isopropoxy group, an allyloxy group, an n-butoxy group, an isobutoxy group, a sec-butoxy group and a tert-butoxy group.

Examples of an acyl group having 1 to 4 carbon atoms include an acetyl group, a propanoyl group and a butanoyl group.

Examples of an acylamino group having 1 to 4 carbon atoms include an acetylamino group, a propanoylamino group and a butanoylamino group.

Examples of an alkylthio group having 1 to 4 carbon atoms include a methylthio group, an ethylthio group and a propylthio group.

Examples of a perfluoroalkyl group having 1 to 4 carbon atoms include a trifluoromethyl group and a pentafluoroethyl group.

Examples of a perfluoroalkyloxy group having 1 to 4 carbon atoms include a trifluoromethoxy group and a pentafluoroethoxy group.

Examples of an alkoxycarbonyl group having 1 to 4 carbon atoms include a methoxycarbonyl group and an ethoxycarbonyl group.

Examples of an alkyl group having 1 to 4 carbon atoms which may be substituted include a methyl group, an ethyl group, an n-propyl group, an isopropyl group, an n-butyl group, an isobutyl group, a sec-butyl group, a tert-butyl group, and these groups having 1 to 4 of groups as substituents selected from the group consisting of halogen atoms, a hydroxyl group, an amino group, a nitro group, a cyano group, a phenyl group and a heterocyclic ring.

Examples of a phenylenediamine derivative include 1,2-phenylenediamine, 4-chloro-1,2-phenylenediamine, 2,3-diaminophenol, 3-methyl-1,2-phenylenediamine, 3-acetyl-1,2-phenylenediamine, 3-acetoamino-1,2-phenylenediamine, 3-methylthio-1,2-phenylenediamine, 4-trifluoromethyl-1,2-phenylenediamine, 4-trifluoromethoxy-1,2-phenylenediamine, methyl 2,3-diaminobenzoate, 1,3-phenylenediamine, 5-chloro-1,3-phenylenediamine, 4-chloro-1,3-phenylenediamine, 2,4-diaminophenol, 2,6-diaminotoluene, 2,4-diaminotoluene, 2,4-diaminoanisole, 2-ethoxy-1,3-phenylenediamine, 4-ethoxy-1,3-phenylenediamine, 5-trifluoromethyl-1,3-phenylenediamine, ethyl 3,5-diaminobenzoate, 1,4-phenylenediamine, 2-chloro-1,4-phenylenediamine, 2,5-diaminophenol, 2,5-diaminotoluene and 2,5-diaminoanisole.

The amount of the phenylenediamine derivative for use in a reaction is in the range of 1 to 10 equivalents, preferably 1 to 8 equivalents with respect to a benzoic acid derivative.

As techniques for converting the benzoic acid derivative into a benzoylimidazole derivative, the following methods can be used:

i) a method which comprises converting the benzoic acid derivative into an acid chloride derivative by the use of oxalyl chloride, thionyl chloride, phosphorus oxychloride or phosgene, and then reacting the acid chloride derivative with imidazole, ii) a method which comprises converting the benzoic acid derivative into a mixed acid anhydride by the use of isobutyl chloroformate or methanesulfonyl chloride, and then reacting the mixed acid anhydride with imidazole, iii) a method which comprises activating the benzoic acid derivative with a peptide condensation agent such as dicyclohexylcarbodiimide, diphenylphosphoric acid azide, diethylphosphoric acid cyanide or 2-chloro-1,3-dimethylimidazolinium chloride, and then reacting the activated compound with imidazole, and iv) a method which comprises reacting the benzoic acid derivative with N,N'-carbonyldiimidazole.

Examples of the acid for use in the activation of a condensation reaction of the benzoylimidazole derivative and the phenylenediamine derivative include inorganic acids such as hydrochloric acid, hydrobromic acid, sulfuric acid and phosphoric acid, organic acids such as acetic acid, lactic acid, tartaric acid, malic acid, succinic acid, fumaric acid, maleic acid, citric acid, benzoic acid, trifluoroacetic acid, trichloroacetic acid, p-toluenesulfonic acid and methanesulfonic acid, Lewis acids such as titanium tetrachloride, aluminum chloride, boron trifluoride, trimethylsilyl iodide, and strong acidic ion exchange resins.

The amount of the acid for use in the reaction is in the range of 0.5 to 10 equivalents, preferably 0.7 to 4 equivalents with respect to a benzoic acid derivative.

Examples of a reaction solvent include aromatic hydrocarbons such as benzene and toluene, ethers such as tetrahydrofuran, dioxane, diethyl ether and 1,2-dimethoxyethane, esters such as ethyl acetate and butyl acetate, halogenated hydrocarbons such as methylene chloride, chloroform and 1,2-dichloroethane, ketones such as acetone and methyl ethyl ketone, N,N-dimethylformamide, N,N-dimethylacetamide, N-methyl-2-pyrolidone, 1,3-dimethyl-2-imidazolidinone, dimethyl sulfoxide, pyridine, acetonitrile and mixtures thereof.

The reaction can be carried out at a temperature of −20° C. to 120° C., preferably −10° C. to 40° C.

The monoacylated phenylenediamine derivative produced by the reaction can be isolated and purified from the reaction mixture by a usual separating means such as extraction, recrystallization or column chromatography.

The monoacylated phenylenediamine means a compound in which only one of two amino groups of the phenylenediamine is acylated.

The monoacylated phenylenediamines which can be manufactured by the process of the present invention are useful as medicines, agricultural chemicals, animal drugs, general-purpose chemicals and intermediates thereof. Above all, the monoacylated phenylenediamines are useful as medicines, especially as therapeutic agents and/or improvement agents for diseases regarding cell proliferation and homeostasis of organisms, drugs for enhancing the effect of gene therapy, and immunosupprresive agents.

Here, examples of the diseases regarding the cell proliferation and the homeostasis of the organisms include malignant tumor, autoimmune disease, dermatosis, vascular disease, hematic disease, infectious disease, allergic disease, gastrointestinal injury, hormonal disease, metabolic disease, diabetes and cachexia.

Examples of the malignant tumor include hematopoietic organ tumors such as acute leukemia, chronic leukemia, malignant lymphoma, multiple myeloma and macroglobulinemia, and solid tumors such as colorectal cancer, cerebral tumor, head and neck cancer, carcinoma mammae, lung cancer, esophageal cancer, stomach cancer, hepatic cancer, gall bladder cancer, biliary cancer, pancreatic cancer, pancreatic island cell cancer, renal cell cancer, adrenocortical cancer, urinary bladder cancer, prostatic cancer, orchioncus, ovarian cancer, uterine cancer, choriocarcinoma, thyroid carcinoma, malignant carcinoid tumor, skin cancer, malignant melanoma, osteosarcoma, soft part cell sarcoma, neuroblastoma, Wilms and retinoblastoma.

Examples of the autoimmune disease includes rheumatism, nephritis, diabetes, systemic lupus erythematosus, human autoimmune lymphocyte proliferative lymphadenopathy, immune blast cell lymphadenopathy, Crohn's disease and chronic ulcerative colitis.

Examples of the dermatosis include psoriasis, acne, eczema, hives, dermatitis, atopic dermatitis, physiological dermatosis, defluvium capillorum, purulent dermatosis and sclerema.

Examples of the vascular disease include arteriosclerosis and restenosis.

Examples of the hematic disease include hyperlipemia, hemolytic anemia, anaplastic anemia and crescent cell anemia.

The infectious disease means a disease caused by the infection of various bacteria, virus and parasite.

Examples of the hormonal disease include the decrease of the homeostasis of organisms caused by a deficiency or an excess of hormone amount, the disorder of metabolism, cell differentiation and reproductivity, hypoplasia and excess hyperergasia.

Examples of the metabolic disease include the decrease of homeostasis of organisms caused by a deficiency or an excess of vitamin amount, the disorder of metabolism, cell differentiation and reproductivity, hypoplasia and excess hyperergasia.

The cachexia is an exhausted state seen during the progress of a chronic disease, and its examples include noticeable weight loss and anemia.

Examples of the effect enhancement of the gene therapy include the efficient transduction of a genetic vector, and the acceleration of the expression of the transduced gene.

The salts of the benzoic acid derivatives represented by the formulae (9) to (11) can be obtained by reactions for preparing the compounds represented by the formulae (9) to (11), but these salts can be easily formed from an acid and a base. Examples of the acid include inorganic acids such as hydrochloric acid, hydrobromic acid, sulfuric acid and phosphoric acid, and organic acids such as acetic acid, lactic acid, tartaric acid, malic acid, succinic acid, fumaric acid, maleic acid, citric acid, benzoic acid, trifluoroacetic acid, trichloroacetic acid, p-toluenesulfonic acid and methanesulfonic acid. Examples of the base include inorganic bases such as lithium hydroxide, sodium hydroxide, potassium hydroxide, calcium hydroxide, aluminum hydroxide, sodium carbonate and potassium carbonate, and an organic base such as DBU.

The selective monoacylation reaction of phenylenediamine in the present invention is widely applicable to not only the benzoic acid derivative represented by the formula (1) but also aromatic heterocyclic carboxylic acid derivatives such as nicotinic acid. Furthermore, a diamine is not limited to phenylenediamine, and many diamines are widely applicable. Examples of the diamines include 1,2-diaminonaphthalene, 1,3-diaminonaphthalene, 1,5-diaminonaphthalene, 1,8-diaminonaphthalene, 2,3-diaminonaphthalene, 9,10-diaminophenanthrene, 1,3-diaminoxylene, 1,4-di(aminomethyl)-cyclohexane, 1,2-ethylenediamine, 1,3-diaminopropane and 1,4-diaminobutane.

Next, the present invention will be described in detail in accordance with examples, but the scope of the present invention should not be limited by these examples.

Incidentally, the selectivity of a reaction was determined on the basis of an area ratio of peaks of eluted components which were obtained by carrying out analysis through high performance liquid chromatography (HPLC) under the following conditions:

HPLC: Shimazu LC-10A (Product by Shimazu Co. Ltd.)

Mobile phase: Acetonitrile:10 mM $KH_2PO_4$=1:2

Flow rate: 1.5 ml/min

Column: YMC-AM312

Column Temperature: 40° C.

Detected UV: 254 nm

EXAMPLE 1

Synthesis of 4-[N-(pyridin-3-ylmethoxycarbonyl)-aminomethyl]benzoic acid

A N,N-dimethylformamide (150 ml) solution including 65.4 g (0.6 mole) of 3-pyridinemethanol was added dropwise to a N,N-dimethylformamide (300 ml) suspension including 97.2 g (0.6 mole) of N,N'-carbonyldiimidazole at an internal temperature of 10° C. or less. The mixture was then added dropwise to a separately prepared 1 N aqueous sodium hydroxide solution (455 ml) including 75.5 g (0.5 mole) of 4-aminomethylbenzoic acid, followed by stirring at room temperature for 6 hours. To the resultant reaction mixture, a saturated sodium chloride solution was added, and concentrated hydrochloric acid was further added, thereby neutralizing the solution. After aging at 5° C. for 2 hours, the deposited white solid was collected by filtration, washed with water and methanol, and then dried to obtain 140 g (yield: 98%) of 4-[N-(pyridin-3-ylmethoxycarbonyl) amino-methyl]benzoic acid.

Analysis data of the product $^1$H NMR δ ppm (DMSO-$d_6$): 4.28 (2H, d, J=5.9 Hz), 5.10 (2H, s), 7.3–7.5 (3H, m), 7.7–8.1 (4H, m), 8.5–8.7 (2H, m).

IR (KBr) cm$^{-1}$: 3043, 1718, 1568, 1434, 1266, 1108, 1037, 984, 756

EXAMPLE 2

Synthesis of 4-[N-(pyridin-3-yl)oxyacetylamino-methyl]benzoic acid 32 g (0.19 mole) of methyl 2-(pyridin-3-yloxy)-acetate, 27 g (0.18 mole) of 4-aminomethylbezoic acid and 59 g (0.39 mole) of DBU were added to ethanol (350 ml), and reaction was then carried out at room temperature for 24 hours. After the reaction mixture had been concentrated, partition was carried out between toluene and water. Concentrated hydrochloric acid was added to the resultant aqueous layer to accomplish neutralization, and a deposited solid was collected by filtration, washed with water and methanol, and then dried to obtain 46 g (yield: 89%) of 4-[N-(pyridin-3-yl)oxyacetylaminomethyl]benzoic acid.

Analysis data of the product $^1$H NMR δ ppm (DMSO-$d_6$): 4.41 (2H, d, J=6.3 Hz), 4.68 (2H, s), 7.32–7.42 (4H, m), 7.88 (2H, d, J=8.2Hz), 8.21 (1H, dd, J=1.6, 4.3 Hz), 8.35 (1H, d, J=2.3 Hz), 8.79 (1H, t, J=6.3 Hz), 12.9 (1H, brs).

IR (KBr) cm$^{-1}$: 3333, 1675, 1539, 1433, 1286, 1237, 1109, 849, 755

EXAMPLE 3

Synthesis of 4-[N-(pyridin-3-yl)oxamoylamino-methyl]benzoic acid 0.5 g (2.6 mmole) of ethyl N-(pyridin-3-yl)oxamate ester, 0.36 g (2.4 mmole) of 4-aminomethylbezoic acid and 0.76 g (5 mmole) of DBU were added to ethanol (5 ml), and reaction was then carried out at room temperature for 24 hours. After the reaction mixture had been concentrated, partition was carried out between toluene and water. Concentrated hydrochloric acid was added to an aqueous layer to accomplish neutralization, and a deposited solid was collected by filtration, washed with water and methanol, and then dried to obtain 0.3 g (yield; 38%) of 4-[N-(pyridin-3-yl)oxamoylaminomethyl]benzoic acid.

Analysis data of the product $^1$H NMR δ ppm (DMSO-$d_6$): 4.48 (2H, d, J=6.3 Hz), 7.37–7.39 (1H, m), 7.43 (2H, d, J=8.2 Hz), 7.92 (2H, d, J=7.9 Hz), 8.20–8.24 (1H, m), 8.33–8.35 (1H, m), 9.01 (1H, d, J=2.3 Hz), 9.69 (1H, t, J=6.3 Hz).

IR (KBr) cm$^{-1}$: 3283, 1895, 1663, 1518, 1414, 1285, 1105, 746

EXAMPLE 4

Synthesis of 4-[N-(pyridin-3-ylmethoxycarbonyl)-aminomethyl]benzoyl chloride hydrochloride 0.8 ml of N,N-dimethylformamide was added to a toluene suspension (2000 ml) including 40 g (0.14 mole) of 4-[N-(pyridin-3-ylmethoxycarbonyl)aminomethyl]benzoic acid. Then, 24 ml of oxalyl chloride were added dropwise to the resultant mixture, followed by stirring for 4 hours. A deposited white solid was collected by filtration to obtain 47.7 g (quantitative) of 4-[N-(pyridin-3-ylmethoxycarbonyl) aminomethyl]benzoyl chloride hydrochloride.

EXAMPLE 5

Synthesis of 1-{4-[N-(pyridin-3-ylmethoxycarbonyl)-aminomethyl]benzoyl}imidazole 1 g (2.9 mmole) of 4-[N-(pyridin-3-ylmethoxycarbonyl) aminomethyl]benzoyl chloride hydrochloride was added to a tetrahydrofuran (10 ml) solution including 0.6 g (8.8 mmole) of imidazole, followed by stirring for 1 hour. A deposited imidazole hydrochloride was removed by filtration, and the reaction solution was then concentrated. Ethyl acetate and water were added to the solution to carry out partition, and the organic layer was then treated in an ordinary manner to obtain 0.54 g (yield: 55%) of 1-{4-[N-(pyridin-3-ylmethoxycarbonyl)aminomethyl]benzoyl}imidazole.

Analysis data of the product

H NMR (270 MHz, DMSO-$d_6$) δ ppm: 4.35 (2H, d, J=5.9 Hz), 5.11 (2H, s), 7.16–7.19 (1H, m), 7.40–7.44 (1H, m), 7.49 (2H, d, J=8.2 Hz), 7.67–7.69 (1H, m), 7.79–7.83 (3H, m), 8.05 (1H, t, J=6.2 Hz), 8.20 (1H, s), 8.54 (1H, dd, J=1.6, 4.6 Hz), 8.16 (1H, d, J=1.6 Hz).

IR (KBr) cm$^{-1}$: 3213, 3016, 1713, 1692, 1607, 1582, 1303, 1275, 901, 752, 719

EXAMPLE 6

Synthesis of N-(2-aminophenyl)-4-[N-(pyridin-3-ylmethoxycarbonyl)aminomethyl]benzamide (an example in which after activation with N,N'-carbonyldiimidazole, an acid was added to carry out reaction)

7.78 g (48 mmole) of N,N'-carbonyldiimidazole were added to a 1,3-dimethyl-2-imidazolidinone (50 g) suspension including 11.45 g (40 mmole) of 4-[N-(pyridin-3-ylmethoxycarbonyl)aminomethyl]benzoic acid. After stirring at room temperature for 2 hours, 17.30 g (0.16 mole) of 1,2-phenylenediamine were added to the solution. After cooling to 2° C., 9.60 g (0.1 mole) of methanesulfonic acid were added dropwise. After stirring for 2 hours, water was added, and the deposited solid was collected by filtration. Purification was then carried out through silica gel column chromatography to obtain 10.83 g (yield: 72%) of N-(2-aminophenyl)-4-[N-(pyridin-3-ylmethoxycarbonyl)aminomethyl]benzamide.

Reaction selectivity based on the result in HPLC

|  | Retention Time/min. | Area % |
| --- | --- | --- |
| Benzoylimidazole as Active Intermediate | 4.3 | 0.00 |
| Monoacylated Phenylenediamine | 4.7 | 98.91 |
| Diacylated Phenylenediamine | 11.7 | 1.09 |

Analysis data of the product mp. 159–160° C.

$^1$H NMR (270 MHz, DMSO-$d_6$) δ ppm: 4.28 (2H, d, J=5.9Hz), 4.86 (2H, s), 5.10 (2H, s), 6.60 (1H, t, J=7.3Hz), 6.78 (1H, d, J=7 Hz), 6.97 (1H, t, J=7 Hz), 7.17 (1H, d, J=8 Hz), 7.3–7.5 (3H, m), 7.78 (1H, d, J=8 Hz), 7.93 (2H, d, J=8 Hz), 8.53 (1H d, J=3.7 Hz), 8.59 (1H, s), 9.61 (1H, s).

IR (KBr) cm$^{-1}$: 3295, 1648, 1541, 1508, 1457, 1309, 1183, 742

EXAMPLE 7

Synthesis of N-(2-aminophenyl)-4-[N-(pyridin-3-ylmethoxycarbonyl)aminomethyl]benzamide (an example in which after an acid chloride was converted into a benzoyl imidazole compound by reaction with imidazole for its activation, an acid was added to carry out reaction using the resulting benzoyl imidazole compound)

1 g (2.9 mmole) of 4-[N-(pyridin-3-ylmethoxycarbonyl)aminomethyl]benzoyl chloride hydrochloride was added to a tetrahydrofuran (20 ml) solution including 0.63 g (9.2 mmole) of imidazole, followed by stirring for 1 hour. After the deposited imidazole hydrochloride had been removed by filtration, a tetrahydrofuran (20 ml) solution including 0.63 g (5.8 mole, 2 equivalents) of 1,2-phenylenediamine and 0.2 ml of trifluoroacetic acid was added at room temperature. After stirring at room temperature for 15 hours, analysis was carried out through HPLC, and a reaction selectivity was determined on the basis of an area ratio of peaks of eluted components.

Reaction selectivity based on the result in HPLC

|  | Retention Time/min. | Area % |
| --- | --- | --- |
| Benzoylimidazole Derivative as Active Intermediate | 4.3 | 0.00 |
| Monoacylated Phenylenediamine | 4.7 | 93.13 |
| Diacylated Phenylenediamine | 11.7 | 6.87 |

EXAMPLE 8

Synthesis of N-(2-aminophenyl)-4-[N-(pyridin-3-ylmethoxycarbonyl)aminomethyl]benzamide (an example in which after an acid chloride was converted into a benzoyl imidazole compound by reaction with imidazole for its activation, an acid was added to carry out reaction using the resulting benzoyl imidazole compound)

The same procedure as in Example 7 was conducted except that 1.26 g (11.6 mmole, 4 equivalents) of 1,2-phenylenediamine were used.

Reaction selectivity based on the result in HPLC

|  | Retention Time/min. | Area % |
| --- | --- | --- |
| Benzoylimidazole Derivative as Active Intermediate | 4.3 | 0.00 |
| Monoacylated Phenylenediamine | 4.7 | 97.25 |
| Diacylated Phenylenediamine | 11.7 | 2.75 |

EXAMPLE 9

Synthesis of N-(2-aminophenyl)-4-[N-(pyridin-3-ylmethoxycarbonyl)aminomethyl]benzamide (an example in which after an acid chloride was converted into a benzoyl imidazole compound by reaction with imidazole for its activation, an acid was added to carry out reaction using the resulting benzoyl imidazole compound)

The same procedure as in Example 7 was conducted except that 2.52 g (23.2 mmole, 8 equivalents) of 1,2-phenylenediamine were used.

Reaction selectivity based on the result in HPLC

|  | Retention Time/min. | Area % |
| --- | --- | --- |
| Benzoylimidazole Derivative as Active Intermediate | 4.3 | 0.00 |
| Monoacylated Phenylenediamine | 4.7 | 98.95 |
| Diacylated Phenylenediamine | 11.7 | 1.05 |

EXAMPLE 10

Synthesis of N-(2-aminophenyl)-4-[N-(pyridin-3-ylmethoxycarbonyl)aminomethyl]benzamide (an example in which after activation with N,N'-carbonyldiimidazole, an acid was added to carry out reaction)

1.5 g (9.2 mmole) of N,N'-carbonyldiimidazole were added to a tetrahydrofuran (30 ml) suspension including 2.5 g (8.7 mmole) of 4-[N-(pyridin-3-ylmethoxycarbonyl) amino-methyl]benzoic acid, followed by stirring at 45° C. for 1 hour. After cooling the solution to room temperature, a tetra-hydrofuran (3 ml) solution including 7.5 g (69 mmole, 8 equivalents) of 1,2-phenylenediamine and 1.2 ml of trifluoroacetic acid was added at room temperature. After reaction at room temperature for 15 hours, analysis was carried out through HPLC, and a reaction selectivity was determined on the basis of an area ratio of peaks of eluted components.

Reaction selectivity based on the result in HPLC

|  | Retention Time/min. | Area % |
| --- | --- | --- |
| Benzoylimidazole Derivative as Active Intermediate | 4.3 | 0.00 |
| Monoacylated Phenylenediamine | 4.7 | 98.57 |
| Diacylated Phenylenediamine | 11.7 | 1.43 |

EXAMPLE 11

Synthesis of N-(2-aminophenyl)-4-[N-(pyridin-3-ylmethoxycarbonyl)aminomethyl]benzamide (an example in which after activation with N,N'-carbonyldiimidazole, an acid was added to carry out reaction)

0.16 g (1 mmole) of N,N'-carbonyldiimidazole was added to a dimethyl sulfoxide (14 ml) solution including 0.28 g (1 mmole) of 4-[N-(pyridin-3-ylmethoxycarbonyl)-aminomethyl]benzoic acid, followed by stirring for 2 hours. After 0.21 g (2 mmole) of 1,2-phenylenediamine had been added, 0.19 ml (2.5 mmole) of trifluoroacetic acid was added dropwise at room temperature. After stirring at room temperature for 5 hours, analysis was carried out through HPLC, and a reaction selectivity was determined on the basis of an area ratio of peaks of eluted components.

Reaction selectivity based on the result in HPLC

|  | Retention Time/min. | Area % |
| --- | --- | --- |
| Benzoylimidazole Derivative as Active Intermediate | 4.3 | 0.00 |
| Monoacylated Phenylenediamine | 4.7 | 97.85 |
| Diacylated Phenylenediamine | 11.7 | 2.15 |

EXAMPLE 12

Synthesis of N-(2-aminophenyl)-4-{2-oxo-2-[(pyridin-3-ylmethyl)amino]ethoxy}benzamide (an example in which after activation with N,N'-carbonyldiimidazole, an acid was added to carry out reaction)

(12-1) 2 g (12 mmole) of ethyl 4-hydroxybenzoate were added to a N,N-dimethylformamide (10 ml) suspension including 0.32 g of sodium hydride under ice cooling. Furthermore, a N,N-dimethylformamide (5 ml) solution including 2.2 g (13 mmole) of ethyl bromoacetate was added dropwise thereto, and reaction was then carried out for 15 hours. After the reaction mixture had been concentrated, partition was carried out between ethyl acetate and water. The organic layer was then treated in an ordinary manner to obtain 2.9 g (yield: 96%) of ethyl 4-(2-ethoxy-2-oxo-ethoxy)benzoate.

Analysis data of the product $^1$H NMR (270 MHz, $CDCl_3$) δ ppm: 1.30 (3H, t, J=7.2 Hz), 1.38 (3H, t, J=7.2 Hz), 4.28 (2H, q, J=7.2 Hz), 4.34 (2H, q, J=7.2 Hz), 4.67 (2H, s), 6.92 (2H, d, J=8.9 Hz), 8.00 (2H, d, J=8.9 Hz).

(12-2) 2.9 g (11 mmole) of ethyl 4-(2-ethoxy-2-oxoethoxy)benzoate, 1.4 g (12 mmole) of 3-picolylamine and 2.1 g (1.3 mmole) of DBU were dissolved in ethanol (12 ml), and reaction was then carried out for 24 hours. After the reaction mixture had been concentrated, partition was carried out between ethyl acetate and water. The organic layer was then treated in an ordinary manner to obtain 3.3 g (yield: 90%) of ethyl 4-{2-oxo-2-[(pyridin-3-ylmethyl)amino]ethoxy}benzoate.

Analysis data of the product $^1$H NMR (270 MHz, DMSO-$d_6$) δ ppm: 1.31 (3H, t, J=6.9 Hz), 4.28 (2H, q, J=6.9 Hz), 4.37 (2H, d, J=6.3 Hz), 4.66 (2H, s), 7.07 (2H, d, J=8.9 Hz), 7.30–7.36 (1H, m), 7.63–7.68 (1H, m), 7.92 (2H, d, J=8.9 Hz), 8.31–8.49 (2H, m), 8.79 (1H, t, J=5.9 Hz).

(12-3) 0.17 g of lithium hydroxide was added to a methanol (30 ml) solution including 1 g (3.2 mmole) of ethyl 4-{2-oxo-2-[(pyridin-3-ylmethyl)amino]ethoxy}benzoate, and reaction was then carried out at 60° C. for 2 hours. After the solvent had been removed, the residue was dissolved in water and then neutralized with hydrochloric acid, and the deposited solid was collected by filtration, washed with water, and then dried to obtain 0.73 g (yield: 79%) of 4-{2-oxo-2-[(pyridin-3-ylmethyl)amino]ethoxy}benzoic acid.

Analysis data of the product

1H NMR (270 MHz, DMSO-$d_6$) δ ppm: 4.37 (2H, d, J=5.9 Hz), 4.65 (2H, s), 7.04 (2H, d, J=8.9 Hz), 7.30–7.35 (1H, m), 7.63–7.68 (1H, m), 7.90 (2H, d, J=8.9 Hz), 8.43–8.49 (2H, m), 8.76 (1H, t, J=5.9 Hz).

(12-4) 0.34 g (2.1 mmole) of N,N'-carbonyldiimidazole was added to a tetrahydrofuran (10 ml) suspension including 0.6 g (2.1 mmole) of 4-{2-oxo-2-[(pyridin-3-ylmethyl) amino]ethoxy}benzoic acid, followed by stirring at 45° C. for 1 hour. After cooling to room temperature, 2.1 g (19.4 mmole, 8 equivalents) of 1,2-phenylenediamine and 0.4 ml of trifluoroacetic acid were added, and reaction was further carried out for 15 hours. After completion of the reaction, a post-treatment was performed in the same manner as in Example 6 to obtain 0.67 g (yield: 53%) of N-(2-aminophenyl)-4-{2-oxo-2-[(pyridin-3-ylmethyl)amino] ethoxy}-benzamide.

Reaction selectivity based on the result in HPLC

|  | Retention Time/min. | Area % |
| --- | --- | --- |
| Benzoylimidazole Derivative as Active Intermediate | 3.4 | 0.00 |
| Monoacylated Phenylenediamine | 3.7 | 98.42 |
| Diacylated Phenylenediamine | 7.5 | 1.58 |

Analysis data of the product mp. 193–195° C.

1H NMR (270 MHz, DMSO-$d_6$) δ ppm: 4.38 (2H, d, J=6.2 Hz), 4.66 (2H, s), 4.87 (2H, s), 6.5–7.7 (8H, m), 7.97 (2H, d, J=8 Hz), 8.4–8.5 (2H, m), 8.79 (1H, m), 9.57 (1H, s).

IR (KBr) cm$^{-1}$: 3403, 1658, 1636, 1508, 1455, 1300, 1250, 755, 716

EXAMPLE 13

Synthesis of N-(2-aminophenyl)benzamide (an example in which after activation with N,N'-carbonyldiimidazole, an acid was added to carry out reaction)

1.62 g (10 mmole) of N,N'-carbonyldiimidazole were added to a dimethyl sulfoxide (10 ml) solution including 1.12 g (10 mmole) of benzoic acid, followed by stirring at room temperature for 1 hour. After the addition of 2.16 g (20 mmole, 2 equivalents) of 1,2-phenylenediamine, 1.9 ml of trifluoroacetic acid were added dropwise at room temperature. After reaction had been further carried out at room temperature for 15 hours, a post-treatment was performed in the same manner as in Example 6 to obtain 1.27 g (yield: 59%) of N-(2-aminophenyl)benzamide.

Reaction selectivity based on the result in HPLC

|  | Retention Time/min. | Area % |
| --- | --- | --- |
| Benzoylimidazole Derivative as Active Intermediate | 5.9 | 0.00 |
| Monoacylated Phenylenediamine | 5.7 | 93.66 |
| Diacylated Phenylenediamine | 27.7 | 6.34 |

Analysis data of the product
mp. 115–116° C.
$^1$H NMR (270 MHz, DMSO-d$_6$) δ ppm: 4.90 (2H, s), 6.56–6.63 (1H, m), 6.78 (1H, dd, J=1.3, 7.9 Hz), 6.94–7.00 (1H, m), 7.17 (1H, J=7.9 Hz), 7.47–7.58 (3H, m), 7.96–8.00 (2H, m), 9.67 (1H, s).

EXAMPLE 14

N-(2-aminophenyl)benzamide was synthesized to inspect a selectivity of reaction (an example in which after activation with N,N'-carbonyldiimidazole, an acid was added to carry out the reaction)

0.81 g (5 mmole) of N,N'-carbonyldiimidazole was added to a 1,3-dimethyl-2-imidazolidinone (10 ml) solution including 0.61 g (5 mmole) of benzoic acid. After stirring at room temperature for 2 hours, 1.08 g (2 equivalents, 10 mmole) of 1,2-phenylenediamine were added to the solution. Furthermore, 1.4 g (12.5 mmole) of trifluoroacetic acid were added dropwise at room temperature. After reaction was carried out at room temperature for 15 hours, analysis was carried out through HPLC, and reactivities were compared on the basis of area ratios of peaks of eluted components.

Reaction selectivity based on the result in HPLC

|  | Retention Time/min. | Area % |
| --- | --- | --- |
| Benzoylimidazole Derivative as Active Intermediate | 5.9 | 0.00 |
| Monoacylated Phenylenediamine | 5.7 | 93.93 |
| Diacylated Phenylenediamine | 27.7 | 6.07 |

EXAMPLE 15

N-(2-aminophenyl)benzamide was synthesized to inspect a selectivity of reaction (an example in which after activation with N,N'-carbonyldiimidazole, an acid was added to carry out the reaction)

The same procedure as in Example 14 was conducted except that 2.16 g (4 equivalents, 20 mmole) of 1,2-phenylenediamine were used.

Reaction selectivity based on the result in HPLC

|  | Retention Time/min. | Area % |
| --- | --- | --- |
| Benzoylimidazole Derivative as Active Intermediate | 5.9 | 0.00 |
| Monoacylated Phenylenediamine | 5.7 | 98.22 |
| Diacylated Phenylenediamine | 27.7 | 1.78 |

EXAMPLE 16

N-(4-aminophenyl)benzamide was synthesized to inspect a selectivity of reaction (an example in which after activation with N,N'-carbonyldiimidazole, the reaction was carried out)

0.81 g (5 mmole) of N,N'-carbonyldiimidazole was added to a dimethyl sulfoxide (10 ml) solution including 0.61 g (5 mmole) of benzoic acid. After stirring at room temperature for 1 hour, 0.54 g (1 equivalent, 5 mmole) of 1,4-phenylenediamine was added. Furthermore, after reaction was carried out at room temperature for 22 hours, analysis was performed through HPLC, and reactivities were then compared on the basis of area ratios of peaks of eluted components.

Reaction selectivity based on the result in HPLC

|  | Retention Time/min. | Area % |
| --- | --- | --- |
| Benzoylimidazole Derivative as Active Intermediate | 5.9 | 0.00 |
| Monoacylated Phenylenediamine | 4.6 | 97.60 |
| Diacylated Phenylenediamine | 19.9 | 2.40 |

EXAMPLE 17

N-(4-aminophenyl)benzamide was synthesized to inspect a selectivity of reaction (an example in which after activation with N,N'-carbonyldiimidazole, the reaction was carried out)

The same procedure as in Example 16 was conducted except that 1.08 g (2 equivalents, 10 mmole) of 1,4-phenylenediamine were used.

Reaction selectivity based on the result in HPLC

|  | Retention Time/min. | Area % |
|---|---|---|
| Benzoylimidazole Derivative as Active Intermediate | 5.9 | 0.00 |
| Monoacylated Phenylenediamine | 4.6 | 99.49 |
| Diacylated Phenylenediamine | 19.9 | 0.51 |

EXAMPLE 18

N-(4-aminophenyl)benzamide was synthesized to inspect a selectivity of reaction (an example in which after activation with N,N'-carbonyldiimidazole, the reaction was carried out)

The same procedure as in Example 16 was conducted except that 2.16 g (4 equivalents, 20 mmole) of 1,4-phenylenediamine were used.

Reaction selectivity based on the result in HPLC

|  | Retention Time/min. | Area % |
|---|---|---|
| Benzoylimidazole Derivative as Active Intermediate | 5.9 | 0.00 |
| Monoacylated Phenylenediamine | 4.6 | 99.78 |
| Diacylated Phenylenediamine | 19.9 | 0.22 |

EXAMPLE 19

N-(3-aminophenyl)benzamide was synthesized to inspect a selectivity of reaction (an example in which after activation with N,N'-carbonyldiimidazole, the reaction was carried out)

0.81 g (5 mmole) of N,N'-carbonyldiimidazole was added to a dimethyl sulfoxide (10 ml) solution including 0.61 g (5 mmole) of benzoic acid. After stirring at room temperature for 1 hour, 0.54 g (1 equivalent, 5 mmole) of 1,3-phenylenediamine was added. Furthermore, after reaction had been carried out at room temperature for 18 hours, analysis was performed through HPLC, and reactivities were then compared on the basis of area ratios of peaks of eluted components.

Reaction selectivity based on the result in HPLC

|  | Retention Time/min. | Area % |
|---|---|---|
| Benzoylimidazole Derivative as Active Intermediate | 5.9 | 0.00 |
| Monoacylated Phenylenediamine | 5.7 | 90.10 |
| Diacylated Phenylenediamine | 25.2 | 9.90 |

EXAMPLE 20

N-(3-aminophenyl)benzamide was synthesized to inspect a selectivity of reaction (an example in which after activation with N,N'-carbonyldiimidazole, the reaction was carried out)

The same procedure as in Example 19 was conducted except that 1.08 g (2 equivalents, 10 mmole) of 1,3-phenylenediamine were used.

Reaction selectivity based on the result in HPLC

|  | Retention Time/min. | Area % |
|---|---|---|
| Benzoylimidazole Derivative as Active Intermediate | 5.9 | 0.00 |
| Monoacylated Phenylenediamine | 5.7 | 94.91 |
| Diacylated Phenylenediamine | 25.2 | 5.09 |

EXAMPLE 21

N-(3-aminophenyl)benzamide was synthesized to inspect a selectivity of reaction (an example in which after activation with N,N'-carbonyldiimidazole, the reaction was carried out)

The same procedure as in Example 19 was conducted except that 2.16 g (4 equivalents, 20 mmole) of 1,3-phenylenediamine were used.

Reaction selectivity based on the result in HPLC

|  | Retention Time/min. | Area % |
|---|---|---|
| Benzoylimidazole Derivative as Active Intermediate | 5.9 | 0.00 |
| Monoacylated Phenylenediamine | 5.7 | 97.25 |
| Diacylated Phenylenediamine | 25.2 | 2.75 |

EXAMPLE 22

Inspection of a reaction accelerating effect by the addition of an acid

Reaction was carried out under the same procedure as in Example 8 without adding any acid. At a time when the reaction was carried out at room temperature for 15 hours, the reaction product was analyzed through HPLC to compare reactivities.

Reaction selectivity based on the result in HPLC

|  | Retention Time/min. | Area % |
|---|---|---|
| Benzoylimidazole Derivative as Active Intermediate | 4.3 | 19.90 |
| Monoacylated Phenylenediamine | 4.7 | 74.35 |
| Diacylated Phenylenediamine | 11.7 | 5.75 |

EXAMPLE 23

Inspection of an effect by the addition of an acid

Reaction was carried out under the same conditions as in Example 14 without adding any acid, and reactivities were then compared. At a time when the reaction was carried out at room temperature for 15 hours, the reaction product was analyzed through HPLC.

Reaction selectivity based on the result in HPLC

|  | Retention Time/min. | Area % |
|---|---|---|
| Benzoylimidazole Derivative as Active Intermediate | 5.9 | 26.97 |
| Monoacylated Phenylenediamine | 5.7 | 63.86 |
| Diacylated Phenylenediamine | 27.7 | 9.17 |

EXAMPLE 24

Inspection of an effect by the addition of an acid

In order to inspect an effect by the addition of an acid, reactions were carried out at room temperature for 1 hour under conditions of Example 21 in the case that no acid was added and in the case that an acid (2.5 equivalents of trifluoroacetic acid) was added, respectively. At a time when each reaction was performed, the resultant reaction product was analyzed through HPLC to compare both the reaction products.

Reaction selectivity based on the result in HPLC

|  | Area % | |
|---|---|---|
|  | Addition of No Acid | Addition of Acid |
| Benzoylimidazole Derivative as Active Intermediate | 32.42 | 0.00 |
| Monoacylated Phenylenediamine | 66.58 | 96.91 |
| Diacylated Phenylenediamine | 1.00 | 3.09 |

Comparative Example 1

4-[N-(pyridin-3-ylmethoxycarbonyl)aminomethyl]-benzoyl chloride hydrochloride was directly reacted with 1,2-phenylenediamine to synthesize N-(2-aminophenyl)-4-[N-(pyridin-3-ylmethoxycarbonyl)aminomethyl]benzamide, and a selectivity of the reaction was inspected.

0.3 g (0.88 mmole) of 4-[N-(pyridin-3-ylmethoxycarbonyl)aminomethyl]benzoyl chloride hydrochloride was added to a tetrahydrofuran (10 ml) solution including 0.38 g (3.5 mmole, 1.4 equivalents) of 1,2-phenylenediamine and 0.25 ml (1.76 mmole) of triethylamine at room temperature. After reaction has been carried out at room temperature for 15 hours, the reaction product was analyzed through HPLC.

Reaction selectivity based on the result in HPLC

|  | Retention Time/min. | Area % |
|---|---|---|
| Monoacylated Phenylenediamine | 4.7 | 79.47 |
| Diacylated Phenylenediamine | 11.7 | 20.53 |

Comparative Example 2

Benzoyl chloride was reacted with 1,2-phenylenediamine to synthesize N-(2-aminophenyl)benzamide, and a selectivity of the reaction was inspected.

0.58 g (5 mmole) of benzoyl chloride was added to a 1,3-dimethyl-2-imidazolidinone (10 ml) solution including 1.08 g (2 equivalents, 10 mmole) or 2.16 g (4 equivalents, 20 mmole) of 1,2-phenylenediamine and 0.7 ml (5 mmole) of triethylamine at room temperature. After reaction was carried out at room temperature for 15 hours, analysis was conducted through HPLC to inspect a selectivity on the basis of an area ratio of peaks of eluted components.

Reaction selectivity based on the result in HPLC

|  | Retention Time/min. | Area % |
|---|---|---|
| Monoacylated Phenylenediamine | 5.7 | 30.10 |
| Diacylated Phenylenediamine | 27.7 | 69.90 |

Comparative Example 3

Benzoyl chloride was reacted with 1,2-phenylenediamine to synthesize N-(2-aminophenyl)benzamide, and a selectivity of the reaction was inspected.

The same procedure as in Comparative Example 2 was conducted except that 2.16 g (4 equivalents, 20 mmole) of 1,2-phenylenediamine were used.

Reaction selectivity based on the result in HPLC

|  | Retention Time/min. | Area % |
|---|---|---|
| Monoacylated Phenylenediamine | 5.7 | 39.12 |
| Diacylated Phenylenediamine | 27.7 | 60.87 |

Comparative Example 4

Benzoyl chloride was reacted with 1,4-phenylenediamine to synthesize N-(4-aminophenyl)benzamide, and a selectivity of the reaction was inspected.

0.58 g (5 mmole) of benzoyl chloride was added to a dimethyl sulfoxide (10 ml) solution including 0.54 g (1 equivalent, 15 mmole), 1.08 g (2 equivalents, 10 mmole) or 2.16 g (4 equivalents, 20 mmole) of 1,4-phenylenediamine and 0.7 ml (5 mmole) of triethylamine at room temperature. After reaction had been carried out at room temperature for 1 hour, analysis was conducted through HPLC to inspect a selectivity on the basis of an area ratio of peaks of eluted components.

Reaction selectivity based on the result in HPLC

|  | Retention Time/min. | Area % |
|---|---|---|
| Monoacylated Phenylenediamine | 4.6 | 38.93 |
| Diacylated Phenylenediamine | 19.9 | 61.07 |

Comparative Example 5

Benzoyl chloride was reacted with 1,4-phenylenediamine to synthesize N-(4-aminophenyl)benzamide, and a selectivity of the reaction was inspected.

The same procedure as in Comparative Example 4 was conducted except that 1.08 g (2 equivalents, 10 mmole) of 1,4-phenylenediamine were used.
Reaction selectivity based on the result in HPLC

|  | Retention Time/min. | Area % |
|---|---|---|
| Monoacylated Phenylenediamine | 4.6 | 49.57 |
| Diacylated Phenylenediamine | 19.9 | 50.43 |

Comparative Example 6

Benzoyl chloride was reacted with 1,4-phenylenediamine to synthesize N-(4-aminophenyl)benzamide, and a selectivity of the reaction was inspected.

The same procedure as in Comparative Example 4 was conducted except that 2.16 g (4 equivalents, 20 mmole) of 1,4-phenylenediamine were used.
Reaction selectivity based on the result in HPLC

|  | Retention Time/min. | Area % |
|---|---|---|
| Monoacylated Phenylenediamine | 4.6 | 50.42 |
| Diacylated Phenylenediamine | 19.9 | 49.53 |

Comparative Example 7

Benzoyl chloride was reacted with 1,3-phenylenediamine to synthesize N-(3-aminophenyl)benzamide, and a selectivity of the reaction was inspected.

0.58 g (5 mmole) of benzoyl chloride was added to a dimethyl sulfoxide (10 ml) solution including 0.54 g (1 equivalent, 5 mmole), 1.08 g (2 equivalents, 10 mmole) or 2.16 g (4 equivalents, 20 mmole) of 1,3-phenylenediamine and 0.7 ml (5 mmole) of triethylamine at room temperature. After reaction was carried out at room temperature for 1 hour, analysis was conducted through HPLC to inspect a selectivity on the basis of an area ratio of peaks of eluted components.
Reaction selectivity based on the result in HPLC

|  | Retention Time/min. | Area % |
|---|---|---|
| Monoacylated Phenylenediamine | 5.7 | 37.97 |
| Diacylated Phenylenediamine | 25.2 | 62.03 |

Comparative Example 8

Benzoyl chloride was reacted with 1,3-phenylenediamine to synthesize N-(3-aminophenyl)benzamide, and a selectivity of the reaction was inspected.

The same procedure as in Comparative Example 7 was conducted except that 1.08 g (2 equivalents, 10 mmole) of 1,3-phenylenediamine were used.
Reaction selectivity based on the result in HPLC

|  | Retention Time/min. | Area % |
|---|---|---|
| Monoacylated Phenylenediamine | 5.7 | 49.57 |
| Diacylated Phenylenediamine | 25.2 | 50.43 |

Comparative Example 9

Benzoyl chloride was reacted with 1,3-phenylenediamine to synthesize N-(3-aminophenyl)benzamide, and a selectivity of the reaction was inspected.

The same procedure as in Comparative Example 7 was conducted except that 2.16 g (4 equivalents, 20 mmole) of 1,3-phenylenediamine were used.
Reaction selectivity based on the result in HPLC

|  | Retention Time/min. | Area % |
|---|---|---|
| Monoacylated Phenylenediamine | 5.7 | 50.42 |
| Diacylated Phenylenediamine | 25.2 | 49.53 |

What is claimed is:

1. A process for preparing a selectively monoacylated phenylenediamine derivative which comprises the steps of converting, into a benzoylimidazole derivative, a benzoic acid derivative represented by the formula (1)

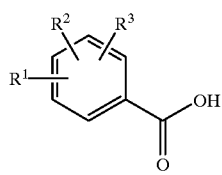

(1)

wherein $R^1$ and $R^2$ are each independently a hydrogen atom, or a substituent selected from the group consisting of a halogen atom, an alkyl group having 1 to 4 carbon atoms, an alkoxy group having 1 to 4 carbon atoms, an acyl group having 1 to 4 carbon atoms, an acylamino group having 1 to 4 carbon atoms, an alkylthio group having 1 to 4 carbon atoms, a perfluoroalkyl group having 1 to 4 carbon atoms, a perfluoroalkyloxy group having 1 to 4 carbon atoms and an alkoxycarbonyl group having 1 to 4 carbon atoms, which substituent is located at an optional position on the benzene ring; and $R^3$ is a hydrogen atom or a substituent which is located at the other optional position than $R^1$ and $R^2$ and is represented by the formula (2)

$$A\text{—}X\text{—}Q\text{—}(CH_2)_n\text{—}$$ (2)

wherein A is a phenyl group or a heterocyclic ring which may be substituted by 1 to 4 groups selected from the group consisting of a halogen atom, a nitro group, a cyano group, an alkyl group having 1 to 4 carbon atoms, an alkoxy group having 1 to 4 carbon atoms, an acyl group having 1 to 4 carbon atoms, an acylamino group having 1 to 4 carbon atoms, an alkylthio group having 1 to 4 carbon atoms, a perfluoroalkyl group having 1 to 4 carbon atoms, a perfluoroalkyloxy group having 1 to 4 carbon atoms or an alkoxycarbonyl group having 1 to 4 carbon atoms, a phenyl group and a heterocyclic ring; X is a direct bond or one of structures represented by the formulae (3-1) to (3-7):

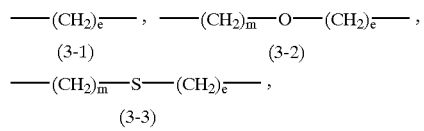

(3)

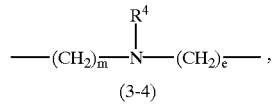

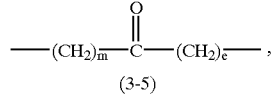

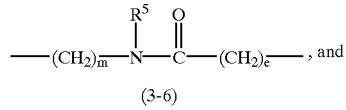

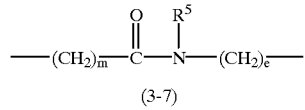

wherein e is an integer of 1 to 4; m is an integer of 0 to 4; $R^4$ is an alkyl group having 1 to 4 carbon atoms which may be substituted or an acyl group represented by the formula (4)

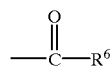

(4)

wherein $R^6$ an alkyl group having 1 to 4 carbon atoms, a perfluoroalkyl group having 1 to 4 carbon atoms, a phenyl group or a heterocyclic ring which may be substituted;

$R^5$ is a hydrogen atom or an alkyl group having 1 to 4 carbon atoms which may be substituted;

Q is a substituent represented by one of the formulae (5-1) to (5-9)

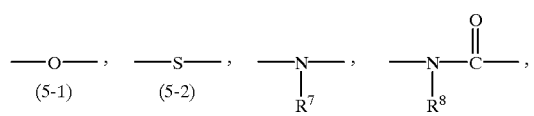

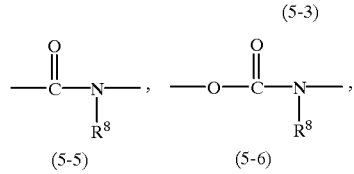

-continued

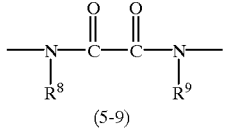

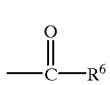

wherein $R^7$ is an alkyl group having 1 to 4 carbon atoms which may be substituted, or an acyl group represented by the formula (6)

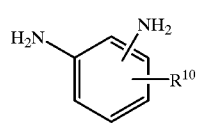

(6)

wherein $R^6$ is as defined above;

$R^8$ and $R^9$ are each independently a hydrogen atom or an alkyl group having 1 to 4 carbon atoms which may be substituted;

and n is an integer of 0 to 4, and then reacting the benzoylimidazole derivative with a phenylenediamine derivative represented by the formula (7)

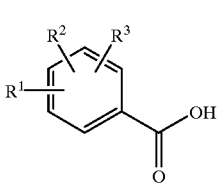

(7)

wherein $R^{10}$ is a hydrogen atom, or a halogen atom, a hydroxyl group, an alkyl group having 1 to 4 carbon atoms, an alkoxy group having 1 to 4 carbon atoms, an acyl group having 1 to 4 carbon atoms, an acylamino group having 1 to 4 carbon atoms, an alkylthio group having 1 to 4 carbon atoms, a perfluoroalkyl group having 1 to 4 carbon atoms, a perfluoroalkyloxy group having 1 to 4 carbon atoms or an alkoxycarbonyl group having 1 to 4 carbon atoms which can substitute at an optional position on a benzene ring, and one of the amino groups can substitute at a remaining optional position on the benzene ring.

2. A process for preparing a selectively monoacylated phenylenediamine derivative according to claim 1 which comprises the steps of converting, into a benzoylimidazole derivative, a benzoic acid derivative represented by the formula (1)

wherein $R^1$, $R^2$ and $R^3$ are as defined above, and then reacting the resultant benzoylimidazole derivative with a phenylenediamine derivative represented by the formula (7)

(7)

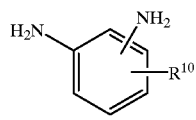

wherein $R^{10}$ is as defined above, in the presence of an acid for activation of the reaction.

3. The process for preparing a monoacylated phenylenediamine derivative according to claim 1 or 2 wherein the benzoic acid derivative is represented by the formula (8)

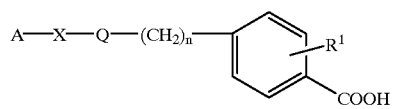

wherein A, X, Q, n and $R^1$ are as defined above.

4. The process for preparing a monoacylated phenylenediamine derivative according to claim 3 wherein A in the formula (8) is a pyridine ring or a condensed pyridine ring which may be substituted.

5. The process for preparing a monoacylated phenylenediamine derivative according to claim 4 wherein n is in the range of 1 to 4.

6. The process for preparing a monoacylated phenylenediamine derivative according to claim 5 wherein $R^1$ is a hydrogen atom.

7. The process for preparing a monoacylated phenylenediamine derivative according to claim 1 or 2 wherein the benzoic acid derivative is represented by the formula (9):

(9)

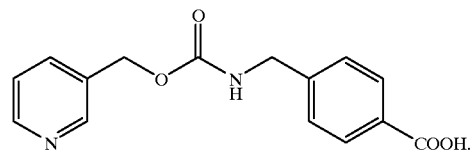

8. The process for preparing a monoacylated phenylenediamine derivative according to claim 1 or 2 wherein the benzoic acid derivative is represented by the formula (10):

(10)

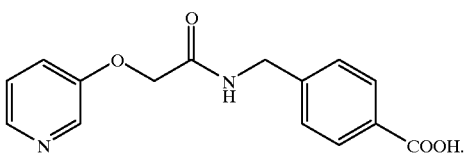

9. The process for preparing a monoacylated phenylenediamine derivative according to claim 1 or 2 wherein the benzoic acid derivative is represented by the formula (11):

(11)

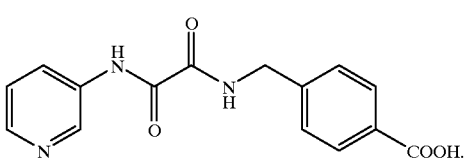

10. The process for preparing a monoacylated phenylenediamine derivative according to claim 1 wherein the phenylenediamine derivative of a reaction material is represented by the formula (12)

(12)

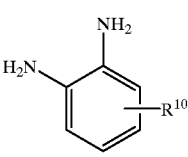

wherein $R^{10}$ is as defined above.

11. The process for preparing a monoacylated phenylenediamine derivative according to claim 10 wherein $R^{10}$ of the formula (12) is a hydrogen atom.

* * * * *